United States Patent [19]

Bell et al.

[11] Patent Number: 4,738,844

[45] Date of Patent: Apr. 19, 1988

[54] MODIFIED (1-28) BETA INTERFERONS

[75] Inventors: Leslie D. Bell, Thame; John C. Smith; Paul G. Boseley, both of High Wycombe, all of England; Michael Houghton, Danville, Calif.

[73] Assignee: G. D. Searle & Co., Chicago, Ill.

[21] Appl. No.: 623,814

[22] Filed: Jun. 22, 1984

[30] Foreign Application Priority Data

Jul. 1, 1983 [GB] United Kingdom ............... 8317880

[51] Int. Cl.[4] ..................... A61K 45/02; C07K 13/00; C07K 15/26; C12P 21/00
[52] U.S. Cl. ..................................... 424/85; 530/351; 435/68; 435/172.3; 435/811
[58] Field of Search ................. 424/85; 435/68, 172.3; 530/351

[56] References Cited

U.S. PATENT DOCUMENTS

| 4,414,150 | 8/1983 | Goeddel | 435/70 |
| 4,569,908 | 2/1986 | Mark et al. | 435/71 |
| 4,588,585 | 5/1986 | Mark et al. | 435/172.3 |

OTHER PUBLICATIONS

Shepard et al., Nature vol. 294, pp. 563-565, 1981.

Primary Examiner—Blondel Hazel
Attorney, Agent, or Firm—Mary Jo Kanady; Paul D. Matukaitis

[57] ABSTRACT

Modified beta interferons containing amino acid substitutions in the beta interferon amino acids 1 to 28 are described. These modified beta interferons exhibit changes in the antiviral, cell growth regulatory or immunomodulatory activities when compared with unmodified beta interferon.

13 Claims, 1 Drawing Sheet

FIG. 1

MODIFIED (1-28) BETA INTERFERONS

BACKGROUND OF THE INVENTION

1. Field of the Invention

Figure 1:
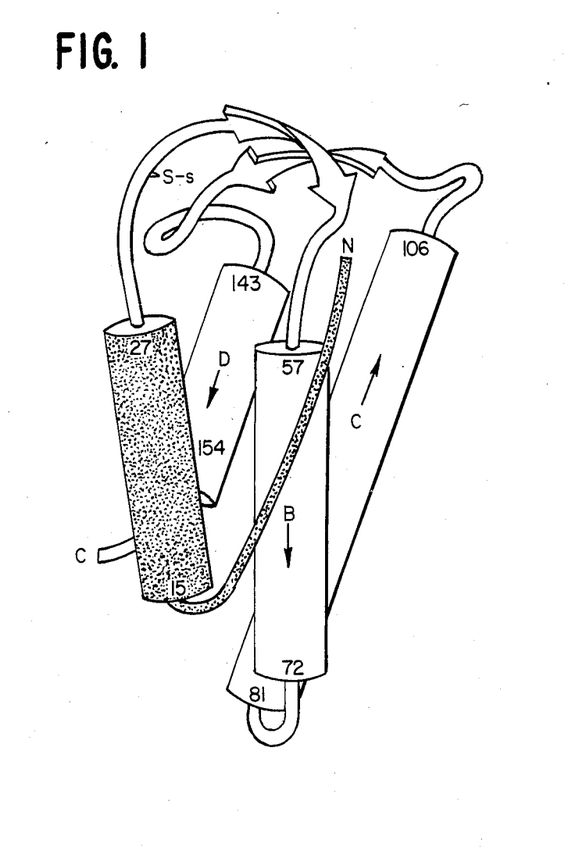

This invention describes the use of recombinant DNA technology for the design and synthesis of novel modified interferons. More specifically the invention relates to interferons not known in nature, which are intended for use in viral and neoplastic diseases, and immunosuppressed and immunodeficient conditions.

2. Description of the Prior Art

The interferons are a class of proteins that occur in vertebrates and act as biological regulators of cell function which include increasing resistance to pathogens, limiting cell growth and modulating the immune system. The most studied property of the interferons is their ability to convert cells into an "antiviral state" during which they are more resistant to virus replication (Lengyel, Annual Review of Biochemistry, 51, 251, 1982). In addition to conferring antiviral resistance to target cells, interferons (IFNs) have antiproliferative (antigrowth) properties (Stewart, 1979, The Interferon System, Springer, Berlin). It has clearly been shown that interferons produced naturally act as antiviral and antiproliferative agents (Gresser et al, Biochim. Biophys. Acta. 516, 231, 1978; J. Exp. Med., 144, 1316, 1976).

The IFNs, by virtue of their antigenic, biological and physico-chemical properties, may be divided into three classes: type I, IFN-α ("leucocyte") and IFN-β ("fibroblast"); and type II, IFN-γ ("immune") (Stewart et al, Nature, 286, 110, 1980). Both genomic DNA and cDNA clones of type I and type II IFNs have been isolated and sequenced, and the potential protein sequences deduced (e.g. Pestka, Arch. Biochem. Biophys., 221, 1, 1983). While in man only one IFN-β and IFN-γ gene are known, human IFN-α is specified by a multigene family comprising at least 20 genes. the classification of IFN-β and IFN-α as type I interferons is in part determined by their significant degree of homology, >23% at the protein level (Taniguchi et al, Nature, 285, 547, 1980).

While the mechanism of action of interferons is not completely understood, certain physiological or enzymatic activities respond to the presence of the interferons. These activities include RNA and protein synthesis. Among the enzymes induced by interferons is (2'-5') (A)n synthetase which is activated by double-stranded RNA. This synthetase generates 2'-5' linked oligonucleotides, and these in turn activate a latent endoribonuclease, RNAase L, which cleaves single-stranded RNA (rRNA). Also induced by IFNs is a protein kinase that phosphorylates at least one peptide chain initiation factor and this inhibits protein synthesis (Lengyel, ibid, p.253). IFNs have been shown to be negative growth regulators for cells by regulation of the (2'-5') An synthetase activity (Creasey et al, Mol. and Cell Biol., 3, 780, 1983). IFN-β was indirectly shown to be involved in the normal regulation of the cell cycle in the absence of inducers through the use of anti-IFN-β antibodies. Similarly, IFNs have been shown to have a role in differentiation (Dolei et al, J. Gen. Virol., 46, 227, 1980) and in immunomodulation (Gresser, Cell. Immunol., 34, 406, 1977). Finally, IFNs may alter the methylation pattern of mRNAs and alter the proportion of fatty acids in membrane phospholipids, thereby changing the rigidity of cell membranes.

These and other mechanisms may respond to interferon-like molecules in varying degrees depending on the structure of the interferon-like polypeptide. Preliminary evidence (UK Patent Application GB 2 090 258A) suggests that members of the multigene IFN-α family vary in the extent and specificity of their antiviral activity (Pestka, ibid.). For example, combination of IFN-αA with IFN-αD resulted in "hybrid" genes which show antiviral properties that are distinct from either parent molecule (Weck et al, Nucl. Acids Res., 9, 6153, 1981). However, hybrid human IFNs with significantly increased human cell activity/specificity have not yet been developed. One Patent has been published describing IFN-β/α hybrids (PCT/US83/00077). This patent describes these examples, none of which have significantly improved activity. The three examples were constructed using two naturally occurring restriction sites. The resulting hybrid interferons were (1) alpha 1 (1-73)-beta (74-166); (2) beta (1-73)-alpha 1 (74-166); and (3) alpha 61A (1-41)-beta (43-166). These three examples differ structurally from the examples of the present invention. These three examples were based upon the accidental location of two restriction sites and not upon the intentionally designed DNA and amino acid sequences of the present invention.

It is envisioned that a modified interferon will display a new advantageous phenotype. The design and synthesis of new interferon-like polypeptides composed of portions of IFN-β and other amino acid sequences is advantageous for the following reasons:

1. New IFNs can be created which show a greater antiproliferative to antiviral activity (and vice versa) resulting from the selective activation of only some of the normal interferon-induced biochemical pathways.
2. The affinity of hybrid or modified IFNs for cell surface receptors will differ from that of naturally occurring interferons. This will allow selective or differential targeting of interferons to a particular cell type, or increased affinity for the receptor—leading to increased potency against a particular virus disease or malignancy.
3. Novel IFNs can be designed which have an increased therapeutic index, thus excluding some of the undesirable side effects of natural IFNs which limit their use (Powledge, T. M., Biotechnology, 2, 214, March 1984).
4. Novel IFNs can include in the design structures which allow increased stability to proteolytic breakdown during microbial synthesis.
5. Novel IFNs can be designed to increase their solubility or stability in vivo, and prevent non-specific hydrophobic interactions with cells and tissues.
6. Novel IFNs can be designed which are more readily recovered from the microbial supernatant or extract, and more easily purified.

Additional Relevant Patent Applications

UK No. GB 2 116 566A—Animal interferons and processes for their production.
U.S. Pat. No. 4 414 150—Hybrid human leucocyte interferons.

SUMMARY OF THE INVENTION

Recombinant DNA technologies were successfully applied to produce modified beta interferon-like polypeptides, nucleic acids (either DNA or RNA) which code for these modified beta interferons, plasmids containing the DNA coding for the modified beta interferons and procedures for the synthesis of these modified beta interferons. Each of the amino acids 1–28 of human beta interferon may individually be replaced by any other amino acid. This replacement may be accomplished in groups of three to twenty-eight amino acids. One preferred embodiment is the replacement of amino acids 1 to 7 of human beta interferon by three to seven other amino acids. Another preferred embodiment is the replacement of beta interferon amino acids 2 to 28 by three to twenty-seven other amino acids. The beta interferon amino acids 1 to 7 and 2 to 28 may be replaced by corresponding human alpha interferon amino acids. Among the alpha interferons are alpha 1, alpha 2 and alpha H. The alpha and beta interferons from any mammal may be used, including but not limited to humans or other primates, horses, cattle, sheep, rabbits, rats, and mice. In one embodiment of the invention, the cysteine occurring at position 16 in human beta interferon may optionally be replaced by serine. Yet another embodiment of the invention discloses the use of the modified beta interferons where in one or more of the antiviral, cell growth regulatory, or immunomodulatory activities is substantially changed from that of the unmodified beta interferon. Particularly preferred embodiments are the amino acid sequences of IFNX401, 412, 413, 414 and 421. Yet another preferred embodiment of the invention is DNA or RNA sequences which code for the synthesis of IFNX401, 412, 413, 414, or 421. Still another embodiment is a plasmid or a cell containing a DNA sequence capable of coding for the synthesis of IFNX401, 412, 413, 414, or 421. Yet another embodiment of the invention is a pharmaceutical composition containing an effective amount of IFNX401, 412, 413, 414, 421. A final embodiment of the invention is the use of pharmaceutical compositions including the modified beta interferons in a method of treating viral infections, regulating cell growth or regulating the immune system.

It was reported that the change of amino acid residue 17 from cysteine to serine markedly increased the specific antiviral activity of IFN-$\beta$ produced in *E. coli* (TNO Interferon meeting, Rotterdam, April 1983). In the present invention this result is not confirmed, and the alterations in biological activity demonstrated by some of the novel IFNs are therefore not due to the $Ser^{17}$. Other amino acids may be present at residue 17, such as cysteine, leucine or alanine. In some modified IFNs (e.g. see Chart 3f) cysteine, leucine or serine may be at position 16. This occurs only where the number of inserted amino acids is one less than the number of IFN-$\beta$ amino acids that are replaced.

An increase in interferon activity can result in an improved therapeutic index. Such an improved therapeutic index reduces or eliminates many of the side effects caused by the use in humans of naturally occurring interferons.

This invention relates to the production in sufficient amounts of novel, highly active, and/or highly specific interferon-like molecules suitable for the prophylactic or therapeutic treatment of humans—notably for viral infections, malignancies, and immunosuppressed or immunodeficient conditions.

BRIEF DESCRIPTION OF THE TABLES AND CHARTS

FIG. 1 shows the predicted structure for $\beta$ and $\alpha_1$ interferons (Sternberg-Cohen)

Chart 2 (a to e) shows the ligated oligonucleotides used in the construction of the novel, modified IFNs.

Chart 3 (a to f) shows the complete nucleotide sequences of the novel, modified IFN genes and the encoded amino acid sequences.

Chart 4 shows the nucleotide sequence of the trp promoter used to initiate transcription of the novel, modified IFN genes.

Table 1 compares expression, antiviral and antiproliferative activity for IFNX414, IFNX421, and IFN-$\beta$ present in crude bacterial extracts.

DESCRIPTION OF THE PREFERRED EMBODIMENTS

Introduction

The IFN-$\beta$ gene is an unique gene but shows some significant homologies to the multigenic IFN-$\alpha$ family (Rubinstein, Biochim. Biophys. Acta, 695, 5, 1982). Sternberg and Cohen (Int. J. Macromol., 4, 137, 1982) have proposed a similar secondary structure for IFN-$\beta$ and IFN-$\alpha_1$. Structure prediction studies suggest four $\alpha$-helices which can be "packed into a right handed bundle (FIG. 1) similar to that observed in several unrelated protein structures as determined by X-ray crystallography. The design of some of the modified interferons described herein is derived from our interpretation of the Sternberg/Cohen model. Since IFNs $\beta$ and $\alpha$ are believed to bind to the same receptor at the cell surface it is possible to introduce variability into IFN-$\beta$ by replacing specific areas with IFN-$\alpha$ segments. The construction of IFNs X401, X412, X413, X414 and X421 resulted in novel, hybrid interferons with altered biological properties. All these interferons were active to some degree, suggesting a large measure of variability in the nature of the inserted amino acid sequence which would give rise to an active molecule.

Accordingly, the field of the present invention is the design, synthesis and characterization of interferon-like molecules related to IFN-$\beta$ which may have amino acid sequences between IFN-$\beta$ residues 1 and 28 replaced with any other amino acid sequence, unrelated protein sequences, or sequences similar to those of IFN-$\alpha$'s, IFN-$\beta$'s found in mammals and other vertebrates.

Each amino acid in the 1 to 28 region can be replaced by any other naturally occurring amino acid. The naturally occurring amino acids and their nomenclature are: alanine (Ala or A); valine (Val or V); leucine (Leu or L); isoleucine (Ile or I); proline (Pro or P); phenylalanine (Phe or F); tryptophan (Trp or W); methionine (Met or M); glycine (Gly or G); serine (Ser or S); threonine (Thr or T); cysteine (Cys or C); tyrosine (Tyr or Y); asparagine (Asn or N); glutamine (Gln or Q); aspartic acid (Asp or D); glutamic acid (Glu or E); lysine (Lys or K); arginine (Arg or R); and histidine (His or H).

Though binding of hybrid IFN-$\alpha$'s ($\alpha_1$ and $\alpha_2$ in Streuli et al, Proc. Natl. Acad. Sci. USA, 78, 2848, 1981), an attempt was made to analyse the number and nature of idiotypes involved in the receptor binding site of IFN-$\alpha$'s. Two sites were proposed as constituting the binding site, one in the amino-terminal half and the other in the carboxy-terminal half of IFN$\alpha$. The two major regions of partial homology between IFN-α's and IFN-β occur between amino acid residues 28-80 and 115-151 which may well correspond to the above mentioned idiotypes.

The relative antiviral (AV) and antiproliferative (AP) activities of the above mentioned IFN-α's and hybrids between them (A, D, A/D and D/A) have been intensively studied in several laboratories (e.g. Weck et al, Nucl. Acids Res., 9, 6153, 1981). The data showed that human cell AP and AV potency can be determined by the first 61 amino acids, but the magnitude of the response clearly depended on the particular IFN-α sequence forming the rest of the molecule (De La Maza et al, J. IFN Res., 3, 359, 1983).

Limited exopeptidase digestion studies implied that IFN-β was less sensitive than IFN-α's to removal of amino-terminal amino acids, but the extent of digestion was not measured. In contrast, removal of amino-terminal amino acids 2-6 of IFN-β was suggested to result in a loss of most of the antiviral activity. Thus, as previously suggested, the amino-terminal region of IFN-β may be important for function.

The nomenclature of the modified interferons are exemplified in the present invention by IFNX401 (IFN-β[$β^{2-7} \rightarrow α_2^{1-5}$]). This abbreviation denotes that amino acid residues 2-7 of IFN-β were replaced by residues 1-5 of IFN-$α_2$. The following examples are to illustrate the invention, and are not intended to limit the scope of the invention in any way. Below are described techniques used in the design, chemical synthesis and insertion of DNA fragments in the 1-28 region of the human IFN-β gene. The resultant novel, modified IFNs are hereafter described as group I IFNs. Increased antiproliferative activity is one of the altered properties shown by some of the group I IFNs with amino acid replacements in the 1-28 region. The techniques described will be familiar to anyone skilled in the art—e.g. see also Molecular Cloning, A Laboratory Manual, eds. Maniatis et al, Cold Spring Harbor Laboratory.

Design of the synthetic gene fragments

The nucleotide sequences of each synthetic DNA fragment (Charts 2a-2e) were designed utilizing the following criteria:
1. Codon utilization (where it deviates from natural IFN-β gene sequence) was optimized for expression in *E. coli*. Natural IFN-β gene sequences were used as far as possible in order to obtain levels of expression of novel IFNs as high as that of IFN-β from plasmid pGC10 (see Table 1). pGC10 (~4,440bp) expresses the natural IFN-β gene at a high level and is identical to p1/24 except for the ribosome binding site sequence shown in Chart 4 and the deletion of the ~546bp BglII-BamHI fragment.
2. Sequences which might anneal to each other in the assembly of the chemically synthesized fragments (Chart 2) were not included in the design (within the limits allowed by the redundancy in the genetic code).

Chemical Synthesis of Gene Fragments

Oligodeoxyribonucleotides were synthesized by the phosphoramidite method (M. H. Caruthers, in "Chemical and Enzymatic synthesis of Gene Fragments", ed. H. G. Gasen and A. Lang, Verlag chemie, p.71, 1982) on controlled pore glass (H. Koster et al, Tetrahedron, 40, 103, 1984). Fully protected 2'-deoxyribonucleotide 3'-phosphoramidites were synthesized from the protected deoxyribonucleotide and chloro-N,N-(diisopropylamino)methoxyphosphine (L. J. McBride and M. H. Caruthers, Tetrahedron Lett., 24, 245, 1983 and S. A. Adams et al, J. Amer. Chem. Soc., 105, 661, 1983). Controlled pore glass supports were synthesised as described (F. Chow et al, Nucl. Acids Res., 9, 2807, 1981) giving 30-50 μmol deoxynucleoside per gram.

The functionalised controlled pore glass (50 mg) was treated in a sintered glass funnel at ambient temperature sequentially with:
1. dichloromethane (3 ml, 10s)
2. 3% (v/v) dichloroacetic acid in dichloromethane (2 ml, 120s)
3. dichloromethane (3 ml, 10s)
4. anhydrous acetonitrile (3 ml, 10s)
5. phosphoramidite monomer (0.06M)/tetrazole (0.23M) in anhydrous acetonitrile (1 ml, 120s)
6. acetonitrile (3 ml, 10s)
7. dimethylaminopyridine (0.07M) in acetic anhydride/2,6-lutidine/acetonitrile (1/2/6 v/v) (1 ml, 60s)
8. acetonitrile (3 ml, 10s)
9. iodine (0.2M) in 2,6-lutidine/tetrahydrofuran/water (1/2/2 v/v) (1 ml, 30s)
10. acetonitrile (3 ml, 10s)

The cycle was repeated with the appropriate phosphoramidite monomer until the oligonucleotide chain was complete. The coupling efficiency of each cycle was monitored by spectrophotometric assay of the liberated dimethoxytrityl alcohol in 10% (w/v) trichloroacetic acid/dichloromethane at 504 nm. After completion of the synthesis, the protecting groups were removed and the oligonucleotide cleaved from the support by sequential treatment with 3% (v/v) dichloroacetic acid/dichloromethane (120s), thiophenol/triethylamine/dioxan (1/1/2 v/v) (1h) and concentrated ammonia at 70° C. (4h). The deprotected oligonucleotides were purified either by HPLC on a Partisil 10 SAX column using a gradient from 1M to 4M triethylammonium acetate pH4.9 at 50° C. or by electrophoresis on a denaturing 15% polyacrylamide gel (pH8.3).

Ligation of Oligonucleotide Blocks 500 pmole aliquots of the oligonucleotides were phosphorylated with 1 unit of T4 induced polynucleotide kinase in 20 μl of a solution containing 1000 Ci/pmole [$^{32}$pγ-ATP (2.5 Ci/mMole), 100 μM spermidine, 20 mM DTT, 10 mM MgCl$_2$, 50 mM Tris-HCl (pH9.0) and 0.1 mM EDTA for 60 minutes at 37° C. The mixtures were then lyophilized and each oligonucleotide purified in a denaturing 15% polyacrylamide gel (pH8.3). After elution from the gel, the recovery was determined by counting the radioactivity.

Blocks (length 30-50 bases) were assembled by combining 25 pmole of each phosphorylated component with equimolar amounts of the unphosphorylated oligomers from the complementary strand. The mixtures were lyophilized and then taken up in 15 μl water and 2 μl 10×ligase buffer (500 mM Tris-HCl pH7.6, 100 mM MgCl$_2$). The blocks were annmealed at 100° C. for 2 minutes, then slowly cooled to room temperature (20° C.). 2 μl 200 mM DTT and 0.5 μl 10 mM ATP were added to give final concentrations of 20 mM DTT and 250 μM ATP in 20 μl. 1.25 units of T4 DNA ligase were also added. After 18 hours at 20° C., the products were purified in a 15% polyacrylamide gel under denaturing conditions.

Two duplex blocks were then constructed from the single-stranded pieces. (These were 150 base pairs and 75 base pairs). 1.5 pmole of each block were taken and the mixtures lyophilized. Annealing was carried out in 15 μl water and 2 μl 10×ligase buffer at 100° C. for 2 minutes, then slowly cooled to 10° C. 2 μl 200 mM DTT, 0.5 μl 10 mM ATP and 1.25 units T4 DNA ligase were added. The reaction was left at 10° C. for 18 hours. The products were then purified in a 10% native polyacrylamide gel.

The final product was assembled by combining 0.4 pmole of the two duplexes. The mixture was lyophilized and then taken up in 15 μl water and 2 μl 10×ligase buffer. It was annealed at 50° C. for 2 minutes and then slowly cooled to 10° C. 2 μl 20 mM DTT, 0.5 μl 10 mM ATP and 1.25 units ligase were then added and the reaction left at 10° C. for 18 hours. the final product was purified in a 5% native polyacrylamide gel. After elution and ethanol precipitation, the product was taken up in 10 μl water. 0.5 μl were removed for counting to calculate the recovery. 2 μl 10×ligase buffer, 2 μl 200 mM DTT, 2 μl 1 mM spermidine, 1 μl 10 mM ATP, 3 μl water and 0.5 units kinase were added to the rest (total volume 20 μl). The reaction was left at 37° C. for 1 hour and stopped by heating at 90° C. for 2 minutes. The final product was ethanol precipitated.

Construction of plasmids expressing novel, modified interferons

This section lists and identifies the vectors employed in the cloning of the synthetic DNA fragments (Chart 2) into the IFN-β coding region, the restriction enzyme sites* used for the insertion, and the rationale for the construction. The positions of these sites* are shown relative to the complete coding nucleotide sequences of the group I novel, modified IFN genes (Chart 3). The IFN-β (or novel IFN) coding region is shown as a heavy line end would be translated from left to right. The vector sequences between the BglII (or BamHI) site and the EcoRI site are the same as those in pAT153 (equivalent to pBR322 with a 705bp HaeII fragment deleted-nucleotides 1,646–2,351 on the map). The E. coli trp promoter (Chart 4) lies between the EcoRI site and ClaI site.

Example 1

IFNX412 IFN-β[β$^{2-7}$→α$_H$$^{1-5*}$][Cys$^{16}$→Ser$^{16}$]

IFNX412 is designed to determine whether substitutions in the β$^{2-7}$ region influence antiproliferative activity. IFN-α$_H$ is the most distinct of the IFN-α's in this region. (*"β$^{2-7}$→α$_H$$^{1-5}$" means that the IFN-β amino acid residues 2–7 inclusive are replaced with IFN-α$_H$ amino acids 1–5 inclusive).

Starting vector: pGC205

This vector contains an entirely synthetic IFN-β gene (Chart 3e) with the Cys$^{17}$→Ser change, inserted between the ClaI-BamHI sites of pl/24C (pl/24C is identical to pl/24*, the plasmid expressing the natural IFN-β gene from the trp promoter, except for the underlined sequences in Chart 4).

*GB 2068 970 A

A synthetic oligonucleotide (Chart 2a) was inserted between the ClaI* and PstI* sites of pGC205 to give the nucleotide sequence shown in Chart 3a. IFNX412 is expressed from plasmid pCH2.

Example 2

IFNX413 IFN-β[β$^{2-7}$→α$_2$$^{1-5}$][Cys$^{16}$→Ser]

IFNX413 was constructed to determine the effect of substituting not only the 2-7 region of IFN-β with an IFN-α$_2$ sequence, but also the Cysteine at residue 16 with serine, on antiproliferative, antiviral and immunostimulating activities, then compared with IFNX401.

Starting vector: pGC205 as above

A synthetic oligonucleotide (Chart 2b) was inserted between the ClaI* and XmaIII* sites of pGC205 to give the nucleotide sequence shown in Chart 3b. IFNX413 is expressed from plasmid pIL122.

Example 3

IFNX414 IFN-β[β$^{3-7}$→α$_2$$^{1-5}$][Cys$^{16}$→Ser]

IFNX414 was constructed to determine the effect of substituting the cysteines at residues 2 and 16 with serines on antiviral, antiproliferative and immunostimulating activities, and compared with IFNX413 (see Example 2).

Starting vector: pGC205 as above

A synthetic oligonucleotide (Chart 2c) was inserted between the ClaI* and XmaIII* sites of pGC205, as for IFNX413 above, to give the nucleotide sequence shown in Chart 3c. IFNX414 is expressed from plasmid pIL121.

Example 4

IFNX421 IFN-β[β$^{3-28}$→α$_1$$^{2-26}$]

This hybrid was constructed to examine the effect of substituting a predicted α-helical segment from IFN-β (Chart 1) with an equivalent segment of IFN-α$_1$ on antiviral, antiproliferative and immunostimulating activities.

Starting vector: pAP4 pAP4 expresses IFN-β and is identical to pGC10 except that the serines at amino acid residues 74 and 75 are coded by TCC and TCG, respectively. These serine codons were changed from TCA and TCT in order to introduce an XhoI site to facilitate the insertion of synthetic DNA. This was accomplished by oligonucleotide-directed mutagenesis (Zoller and Smith, Nucl. Acids Res., 10, 6487, 1982) using the mismatch primer: 5'-CAGTGCTCGAGGAATCTTGTC-3'.

A synthetic oligonucleotide (Chart 2d) was inserted between the ClaI* and XhoI* sites of pAP4 to give the nucleotide sequence of IFNX421 shown in Chart 3d. IFNX421 is expressed from plasmid pNW32.

Example 5

IFNX401 IFN-β[β$^{2-7}$→α$_2$$^{1-5}$]

This hybrid was constructed to examine the effect of inserting IFN-α$_2$ sequences near the amino-terminal region of IFN-β on antiviral, antiproliferative and immunostimulating activities.

Starting vector: pI/24C

Plasmid pI/24C expresses the natural IFN-β gene and is identical to pI/24 except for the ribosome binding site sequence shown in Chart 4.

A synthetic oligonucleotide (Chart 2e) was inserted between the ClaI* and HinfI* sites of pI/24C to give the necleotide sequence shown in Chart 3f. IFNX401 is expressed from plasmid pXX401.

Expression of novel, modified IFNs in Escherichia coli

All of the above mentioned plasmids were grown in E. coli HB101 in the presence of a low level of tryptophan to an OD$_{600}$ of 0.5, then induced for IFN synthesis. The medium (200 ml) contained: M9 salts, 0.5% glucose, 0.1 mM CaCl$_2$, 0.5% Casamino acids, 1 mM MgSO$_4$, 0.1 mg/ml vitamin B$_1$, 2.5 μg/ml tryptophan and 100 μg/ml carbenecillin.

200 ml of medium was inoculated with 2-4 ml of an overnight culture of each clone (in the host E. coli HB101) grown in the above medium except for the presence of 42.5 μg/ml tryptophan, and grown at 37° C. with vigorous aeration. As OD$_{600}$ of 0.5, indole acrylic acid, the inducer of the E. coli trp promoter and therefore also of IFN synthesis, was added to 20 μg/ml. At 4-5 hours after induction 3 ml of culture was withdrawn (OD$_{600}$=0.75-1.2 range) and split as follows: (1) 1 ml was for estimation of total "solubilized" IFN antiviral activity (the activity regained after a denaturation/renaturation cycle); (2) 1 ml was for display of the total accumulated E. coli proteins plus IFN in a polyacrylamide gel; and (3) 1 ml was for estimation of total "solubilized" IFN antiproliferative activity (the activity regained after a denaturation/renaturation cycle).

1. Estimation of TOTAL "solubilized" IFN antiviral activity

For recovery of TOTAL "solubilized" IFN antiviral activity, the pellets were vortexed in 20 μl "lysis buffer" per 0.1 OD$_{600}$ per ml of culture. ("Lysis buffer" is 5M urea, 30 mM NaCl, 50 mM Tris-HCl pH 7.5, 1% SDS, 1% 2-mercaptoethanol, 1% HSA). The mixture was heated for 2-3 min. at 90° C., frozen at −70° C. for 15 min., thawed and centrifuged at 17K rpm for 20 min. The supernatant was diluted in 1 log steps to 1:20$^5$, and appropriate dilutions immediately assayed for IFN antiviral activity by monitoring the protection conferred on Vero cells against the cytopathic effect (cpe) of EMC virus in an in vitro micro-plate assay system (e.g. see Dahl and Degre, Acta. Path. Microbiol. Scan., 1380, 863, 1972). The diluent was 50 mM Tris-HCl pH 7.5, 30 mM NaCl, 1% human serum albumin (HSA).

2. Polyacrylamide gel electrophoresis of total polypeptides

Cells from 1 ml of culture were mixed with 10 μl per 0.1 OD$_{600}$ per ml of final sample buffer: 5M urea, 1% SDS, 1% 2-mercaptoethanol, 50 mM Tris-HCl pH 7.5, 30 mM NaCl and 0.85% bromophenol blue. The mixture was heated at 90° C. for 5 min., centrifuged for 10 min. and 5-7 μl loaded on a 15% acrylamide/0.4% bisacrylamide "Laemmli" gel. Electrophoresis was at 70 V for 18 hours. The gel was fixed and stained with Coomassie brilliant blue, then dried and photographed.

3. Estimation of TOTAL "solubilized" IFN antiproliferative activity

Antiproliferative activity was assessed by the ability of the novel IFN to inhibit the replication of the Daudi (lymphoblastoid) cell line (Horoszewicz et al, Science, 206, 1091, 1979). Daudi cells (in log phase) were cultured for 6 days in 96 well plates in the presence of various dilutions of interferon. The phenol red indicator in the medium changes from red to yellow (more acid) with progressive cell growth. Liquid paraffin was added to prevent pH change on exposure to the atmosphere and the pH change in the medium measured colorimetrically on a Dynatech plate reader. Interferon inhibition of cell growth is reflected by a corresponding reduction in the colour change.

Comparison of IFN protein expression, antiviral activity and antiproliferative activity in bacterial extracts Table 1 sets out the expression levels and antiproliferative and antiviral activities of the group I novel, modified IFNs in crude bacterial extracts. A range of activities may be given, reflecting natural variation in a biological system or assay. The activity quoted is that which is regained after SDS/urea/mercaptoethanol treatment, by diluting the extract in 1% human serum albumin, as above.

It may be seen that both in vitro antiviral and antiproliferative activities of IFNX414 are ~5-fold higher than those of IFN-$\beta$.

TABLE 1

| Novel, modified IFN | IFNX No. | Expression (% of total E. coli protein) | EMC/Vero Antiviral activity IU/L/OD$_{600}$ | Daudi cell Antiproliferative activity U/ml at IC$_{50}$ |
|---|---|---|---|---|
| 1. IFN-$\beta[\beta^{2-7}\rightarrow\alpha_H^{1-5}]$ [Cys$^{16}\rightarrow$Ser] | 412 | n.v.* | 0.65–11 × 10$^6$ | — |
| 2. IFN-$\beta[\beta^{2-7}\rightarrow\alpha_2^{1-5}]$ [Cys$^{16}\rightarrow$Ser] | 413 | n.v.* | 6.7 × 10$^5$ | — |
| 3. IFN-$\beta[\beta^{3-7}\rightarrow\alpha_2^{2-5}]$ [Cys$^{16}\rightarrow$Ser] | 414 | 10 | 1.2 × 10$^9$ | 1.7 × 10$^4$ |
| 4. IFN-$\beta[\beta^{3-28}\rightarrow\alpha_1^{2-26}]$ | 421 | 1–2 | 1.5 × 10$^7$ | <10$^3$ |
| 5. IFN-$\beta$ (control) | — | 10 | 0.5–2.0 × 10$^8$ | 3.4 × 10$^3$ | n.v.* not visible on polyacrylamide gel (Coomassie stain)
U/ml at IC$_{50}$ = dilution of bacterial extract giving 50% cell growth inhibition Biological Properties of IFNX401

1. Methods

IFNX401 was extracted from E. coli with the aid of sodium dodecyl sulphate (SDS) and purified by chromatography on AcA44. IFNX401 had estimated purity of 70–90% based on polyacrylamide gel electrophoretic (PAGE) analysis.

Purified IFNX401 was tested to determine its specific antiviral, antiproliferative and immunomodulatory activities. The following assay systems were employed.

(i) Antiviral assay
  (a) Cytopathic effect (CPE) assay with encephalomyocarditis (EMC) virus. This is a standard assay which measures the ability of interferon to protect cell monolayers against the cytopathic effect of EMC virus. The cell lines used were: Vero (African Green Monkey epithelial), WISH (amnion epithelial), MRC-5 (foetal lung fibroblast) and 17-1 (foetal lung fibroblast). Cell monolayers were established in 96 well flat-bottomed microtitre plates in DMEM medium containing 2% donor calf serum plus glutamine and antibiotics. Serial 1 in 2 dilutions of interferon were incubated with the cells at 37° for 18–24 hours, the supernatant discarded and an appropriate challenge dose of EMC virus in medium added. After incubation at 37° for a further 24 hours, the supernatants were discarded, the monolayers fixed with formol/saline and stained with crystal violet. The plates were read visually to establish the dilution of interferon giving 50% inhibition of the cytopathic effect.
  (b) Plaque reduction assay—using Herpes simplex type 2 (HSV-2) virus with Vero (monkey) Chang (human) and MDBK (bovine cells). Confluent monolayers of cells were established in 96 well flat-bottomed microtitre plates. After incubation at 37° for 18 hours with dilutions of interferons, the cells were challenged with an appropriate number of plaque forming units of virus, overlaid with medium containing 0.5% carboxymethyl cellulose and incubated at 37° for 24 hours. After fixation and staining the plaques were counted microscopically and the counts expressed as a percentage of the mean maximum plaque counts in untreated control wells. Interferon titres are the reciprocal dilutions giving 50% reduction in plaque number/well.

(ii) Antiproliferative assay
  Daudi cells in Dulbecco's Modified Eagles Medium (DMEM) were seeded at $2 \times 10^5$/ml (200 $\mu$l) in 96 well tissue culture plates. Interferons were added at the time of seeding and cells incubated at 37° in a humidified 5% CO$_2$ atmosphere. After 22 hours, tritiated thymidine was added and the cells incubated for a further 2 hours after which they were harvested on a Flow cell harvester washed and treated with 5% trichloroacetic acid. Acid insoluble radioactivity was counted and inhibition of thymidine incorporation was taken as a measure of the antiproliferative activity of interferon.

(iii) Immunomodulatory assay (Natural Killer (NK) Cell Activity)
  Buffy coat cells separated from human peripheral blood by Ficoll/Hypaque sedimentation were suspended in supplemented RPMI 1640 medium and incubated overnight at 37° with interferon dilutions. After washing to remove interferon, these effect or cells were incubated at 37° for a further 4 hours with $^{51}$Cr-labelled K562 cells at effector to target cell ratios of 20:1 to 10:1. (K562 is a human tumour-derived cell line). After centrifugation an aliquot of the supernatant was removed for measurement of released radioactivity. Maximum $^{51}$Cr release was obtained by repeated freeze-thawing of a target cell suspension and a background control obtained by measurement of $^{51}$Cr release from target cells incubated without effector cells. Results were expressed as percentage specific $^{51}$Cr release:

$$\frac{\text{Test sample} - \text{background}}{\text{Maximum release} - \text{background}} \times 100$$

2. Results
  (i) Antiviral activities
    (a) CPE assay—EMC virus

Table 2 lists the assay means for hybrid X401 and the recombinant-derived IFN-$\beta$ measured against EMC virus in Vero and the four human cell lines. The activities are expressed in units/mg protein.

From the individual interferon means in different cell types contained in Table 2 and from the summary pooled data across all cell types it is seen that IFNX401 has activity very similar to that of IFN-$\beta$ in the different cell lines.

TABLE 2

Antiviral activities of recombinant interferons against encephalomyocarditis virus (IFN units/mg protein)
Mean activities in each cell line

| PREPAR-ATION | CELL LINE | | | | |
|---|---|---|---|---|---|
| | Vero | Chang | WISH | MRC-5 | 17-1 |
| IFN-$\beta$ $\bar{x}$ | $1.5 \times 10^5$ | $5.2 \times 10^5$ | $8.4 \times 10^5$ | $1.5 \times 10^5$ | $7.1 \times 10^4$ |
| IFNX401 $\bar{x}$ | $2.8 \times 10^5$ | $6.5 \times 10^5$ | $1.8 \times 10^6$ | $1.7 \times 10^5$ | $7.7 \times 10^4$ |

| PREPARATION | POOLED MEAN | 95% CONFIDENCE LIMITS (u/mg) |
|---|---|---|
| IFN-$\beta$ | $2.4 \times 10^5$ u/mg | $1.5$–$3.9 \times 10^5$ |
| IFNX401 | $1.7 \times 10^5$ u/mg | $1.0$–$3.0 \times 10^5$ |

($\bar{x}$ calculated based upon 3–5 assays)

For comparative purposes, the observed activities (in units/ml) of preparations of fibroblast IFN-$\beta$ and leucocyte IFN-$\alpha$ are shown in Table 3. These natural interferons were not available in purified form and were used in the assays in dilute solutions containing large amounts of non-interferon protein. Thus, results with natural IFN-$\beta$ and IFN-$\alpha$ cannot be quoted in units/mg and the results in Table 3 are not directly comparable with those of Table 2. Nevertheless, it can be seen that the activity of both natural interferons is sustained across the five cell lines within an interferon class with the exception that WISH cells appear slightly more sensitive to both IFN-$\beta$ and IFN-$\alpha$

TABLE 3

Relative antiviral activities of natural interferon preparations against encephalomyocarditis virus in vero and human cell lines

| PREPAR-ATION | Interferon units/ml CELL LINE | | | | |
|---|---|---|---|---|---|
| | Vero | Chang | WISH | MRC-5 | 17-1 |
| Fibroblast-derived $\bar{x}$ | $3.6 \times 10^4$ | $5.6 \times 10^4$ | $1.3 \times 10^5$ | $7.8 \times 10^4$ | $6.8 \times 10^4$ |
| Leucocyte-derived IFN-$\beta$ $\bar{x}$ | $2.5 \times 10^2$ | $1.5 \times 10^2$ | $1.3 \times 10^3$ | 80 | 80 |

(b) Plaque reduction assays HSV-2

Similar estimates of antiviral activities obtained with HSV-2 by means of plaque reduction assays are given in Table 4. In this case the experiments were confined to the human Chang cells, primate Vero cells on bovine MDBK cells. IFNX401 again shows comparable activity to IFN-$\beta$ with each cell type.

The pattern of natural IFN-$\beta$ and IFN-$\alpha$ against HSV-2 in these 3 cell lines is shown in Table 5, again expressed as units/ml rather than as specific activity as a result of impure IFNs. In contrast to some reported results from other laboratories, IFN-$\beta$ reacts reasonably well with our MDBK cell line, producing antiviral activity at about the same dilution as Vero or Chang cells. On the other hand, the IFN-$\alpha$ standard reacted substantially better with MDBK cells than with either Vero or Chang cells.

TABLE 4

Antiviral activities of recombinant interferons against HSV-2 determined by plaque reduction assay

| PREPARATION | Interferon units/mg protein CELL LINE | | |
|---|---|---|---|
| | Vero | Chang | MDBK |
| IFN-$\beta$ $\bar{x}$ | $1.2 \times 10^5$ | $4.7 \times 10^5$ | $2.5 \times 10^5$ |
| IFNX401 $\bar{x}$ | $1.4 \times 10^5$ | $2.2 \times 10^5$ | $1.9 \times 10^5$ |

TABLE 5

Relative antiviral activity of natural interferons against HSV-2 in monkey, human and bovine cells determined by plaque reduction

| PREPARATIONS | Interferon units/ml CELL LINE | | |
|---|---|---|---|
| | Vero | Chang | MDBK |
| Fibroblast-derived IFN-$\beta$ $\bar{x}$ | $2.6 \times 10^4$ | $9.3 \times 10^4$ | $1.9 \times 10^4$ |
| Leucocyte-derived IFN-$\alpha$ $\bar{x}$ | 59 | 90 | $6.8 \times 10^3$ |

Summarizing the results of antiviral activity with RNA and DNA viruses in relevant cell types, Table 6 lists the activities of the recombinant and natural interferons against EMC and HSV-2 in Chang and Vero cells (data from Tables 2–5). There is no indication from these results of preferential activity of IFNX401 against one or other of the 2 virus types. The results from the 2 sets of assays are remarkably similar and are not significantly different. Thus the pooled mean antiviral activity against EMC virus shown in the analysis of variance to Table 2 is equally valid as an estimate of antiherpes activity and can be used as an overall indicator of specific antiviral activity of IFNX401.

TABLE 6

Relative antiviral activity against encephalomyocarditis virus and HSV-2 for recombinant and natural interferons assayed in human and monkey cells

| IFN Preparation | Recombinant interferons (unit/mg protein) | |
|---|---|---|
| | Pooled mean activity EMC virus (from Table 1 analysis) | Pooled mean activity HSV-2 Vero and Chang cells |
| IFN-$\beta$ | $2.4 \times 10^5$ | $3.5 \times 10^5$ |
| IFNX401 | $1.7 \times 10^5$ | $1.8 \times 10^5$ |

(c) Comparative antiviral data with an atypical Chang cell line

One line of Chang conjunctival cells maintained in high passage (approx. X 160) has undergone a mutational change such that it is approximately 3 times more sensitive to IFN-$\beta$ than the normal low passage Chang cells which we have used in routine assays. At the same time, the atypical high passage Chang cells recognize and respond to IFN-$\alpha$ with a 100-fold increase in sensitivity compared to the parental low passage Chang cells. Comparative ratios of antiviral activity in high and low passage Chang cells can therefore be used to indicate a degree of "α-like" property in a particular recombinant. The results of profiling the recombinant IFNX401 in this way is shown in Table 7.

(ii) Antiproliferative activity

IFNX401 was assayed for growth inhibitory activity against Daudi lymphoblastoid cells, in at least 4 replicate assays. The mean results of these assays are given in Table 8, activities being expressed as the protein concentration required to produce a 50% inhibition of maximum thymidine incorporation in untreated control cells (Inhibitory Dose$_{50}$). IFNX401 has slight but significantly increased potency as an antiproliferative agent.

TABLE 7

Antiviral activities of recombinant and natural interferons in atypical Chang cells

| | Chang$^A$ (High passage) | Chang (Routine low passage) | Ratio ChA/Ch |
|---|---|---|---|
| | Units/mg | | |
| IFN-β | $1.6 \times 10^6$ | $5.2 \times 10^5$ | 3 |
| IFNX401 | $1.3 \times 10^6$ | $6.5 \times 10^5$ | 2 |
| | Units/ml | | |
| Fibroblast IFN-β | $1.7 \times 10^5$ | $5.6 \times 10^4$ | 3 |
| Leucocyte IFN-α | $3.4 \times 10^4$ | $1.5 \times 10^2$ | 226 |

TABLE 8

Antiproliferative activity of recombinant interferons assayed in Daudi human lymphoblastoid cells

| PREPARATION | No. of replicate assays (n) | Inhibitory Dose$_{50}$ (μg/ml) Corrected Mean ID$_{50}$ | 95% Confidence Limits |
|---|---|---|---|
| IFN-β | 4 | 3.8 | 1.5–9.8 |
| IFNX401 | 4 | 1.2 | 0.5–3.2 |

(iii) Immunomodulatory activity—NK assay

The recombinant interferons were also repeatedly assayed for ability to enhance natural killer (NK) cell activity, a total of 9–11 assays contributing to the results which are shown in Table 9. In a similar fashion to the antiproliferative activity, the specific NK stimulating activity is expressed as the protein dose concentration producing a 50% effect (Stimulating Dose$_{50}$). IFNX401 displays similar NK stimulating activity to IFN-β.

TABLE 9

Immunostimulant activities of recombinant interferons assayed with human NK cells

| PREPARATION | No. of replicate assays (n) | Corrected Mean SD$_{50}$ | 95% Confidence Limits |
|---|---|---|---|
| IFN- | 11 | 3.4 | 2.1–5.4 |
| IFNX401 | 9 | 4.9 | 2.9–8.3 |

3. Conclusions

Mean specific activities for the antiviral, antiproliferative and immunomodulatory properties of each interferon are summarized in Table 10. (It should be noted that activity varies directly with the figures taken from antiviral assays but inversely with the figures quoted from ID$_{50}$ and SD$_{50}$ assays). For convenience these results have been indexed relative to the IFN-β parent in the lower half of Table 10. From this analysis it will be seen that IFNX401 has identical antiviral and immunostimulant properties to IFN-β but it is 3 times more potent in is antiproliferative activity than IFN-β. This increase in antiproliferative activity is small but significant.

TABLE 10

Comparative summary of biological data for recombinant and natural interferons

| PREPARATION | Specific antiviral activity (u/mg) | Specific antiproliferative activity (ID$_{50}$ μg/ml$^{-1}$) | Specific immunostimulant activity (SD$_{50}$ μg/ml$^{-1}$) |
|---|---|---|---|
| IFN-β | $2.4 \times 10^5$ | 3.8 | 3.4 |
| IFNX401 | $1.7 \times 10^5$ | 1.2 | 4.9 |
| Indexed results (IFN-β = 100) | | | |
| IFN-β | 100 | 100 | 100 |
| IFNX401 | 100 (71) | 316 | 100 (69) |

Figures in brackets indicate actual calculated index where it is not significantly different from 100. In all other cases, differences from 100 are significant.

Pharmaceutical formulation and administration

The novel, modified interferons of the present invention can be formulated by methods well known for pharmaceutical compositions, wherein the active interferon is combined in admixture with a pharmaceutically acceptable carrier substance, the nature of which depends on the particular mode of administration being used. Remington's Pharmaceutical Sciences by E. W. Martin, hereby incorporated by reference, describes compositions and formulations suitable for delivery of the interferons of the present invention. For instance, parenteral formulations are usually injectable fluids that use physiologically acceptable fluids such as saline, balanced salt solutions, or the like as a vehicle. Oral formulations may be solid, e.g. tablet or capsule, or liquid solutions or suspensions.

The novel, modified interferons of the invention may be administered to humans or other animals on whose cells they are effective in various ways such as orally, intravenously, intramuscularly, intraperitoneally, intranasally, intradermally or subcutaneously. Administration of the interferon composition is indicated for patients with malignancies or neoplasms, whether or not immunosuppressed, or in patients requiring immunomodulation, or antiviral treatment. Dosage and dose rates may parallel those employed in conventional therapy with naturally occurring interferons—approximately $10^5$ to $10^8$ units daily. Dosages significantly above or below these levels may be indicated in long term administration or during acute short term treatment. A novel, modified interferon may be combined with other treatments or used in association with othere chemotherapeutic or chemopreventive agents for providing therapy against the above mentioned diseases and conditions, or other conditions against which it is effective.

Modifications of the above described modes for carrying out the invention such as, without limitation, use of alternative vectors, alternative expression control systems, and alternative host micro-organisms and other therapeutic or related uses of the novel interferons, that are obvious to those of ordinary skill in the biotechnology, pharmaceutical, medical and/or related fields are intended to be within the scope of the following claims.

CHART 2a

Chemically synthesized sequence for IFNX412

```
ClaI                            PstI
CGATAAGCTATGTGCAACCTGTCTCAGTTCCTGCA
    TATTCGATACACGTTGGACAGAGTCAAGG
```

CHART 2b

Chemically synthesized sequence for IFNX413

```
ClaI
CGATAAGCTATGTGCGACCTGCCGCAATTCCT
    TATTCGATACACGCTGGACGGCGTTAAGGA

GCAACGTTCTTCTAACTTCCAATCTCAGAA
    CGTTGCAAGAAGATTGAAGGTTAGAGTCTT

ACTGCTGTGGCAACTGAAC
              TGACGACACCGTTGACTTGCCGG
                                 XmaIII
```

CHART 2c

Chemically synthesized sequence for IFNX414

```
ClaI
CGATAAGCTATGTCTGACCTGCCGCAATTCCT
    TATTCGATACAGACTGGACGGCGTTAAGGA

GCAACGTTCTTCTAACTTCCAATCTCAGAA
    CGTTGCAAGAAGATTGAAGGTTAGAGTCTT

ACTGCTGTGGCAACTGAAC
              TGACGACACCGTTGACTTGCCGG
                                 XmaIII
```

CHART 2d

Chemically synthesized sequence for IFNX421

```
ClaI
CGATAAGCTATGTCAGATCTTC CAGAAACCCATTCTC
    TATTCG ATACAGTCTAGAAGGTCTTTG GGTAAGAG

TCGACAACAGACGTACCCTTA TGCTGCT CGCTCAGA
    AGCTGTTGTCTGCA TGGGAATACGACGAGCGAGTCT

TGAGCCGGATATCCCCGGAATATTGCCT CAAGGACA
    ACTCGGCCTATAGGGGCCTTA TAACGGAGTTCCTGT

GGATGAACTTTGACA TCCCTGA GGAGATTAAGCAGCT
    CCTACTTG AAACTGTAGGGACTCCTCTAA TTCGTCGA

GCAGCAGTTTCAGA AAGAGGA CGCCGCA TTGACCATC
    CGTCGTC AAAGTCTTTCTCCT GCGGCGTAACTGGTAG

TATGAGATGCTCCA GAACATCTTTGCTA
    ATACTCT ACGAGGTCTTGTAG AAACGAT

TTTTCAG ACAAGATTCC
              AAAAGTCTGTTCTAAGGAGCT
                               XhoI
```

CHART 2e

Chemically synthesized sequence for IFNX401

```
ClaI
CGATAAGCTATGTGCGACTTACCACA
    TATTCGATACACGCTGAATGGTGTAA
                         HinfI
```

CHART 3a

IFNX412

$$\text{IFN}{-}\beta[\text{IFN}{-}\beta^{2-7} \longrightarrow \text{IFN}{-}\alpha_H^{1-5}] \; [\text{Cys}^{16} \longrightarrow \text{Ser}^{16}]$$

```
         ClaI                    PstI
                5              10              15
(N9)    MET CYS ASN LEU SER GLN PHE LEU GLN ARG SER SER ASN PHE GLN
        ATG TGC AAC CTG TCT CAG TTC CTG CAG CGT TCT TCT AAC TTC CAA 20              25              30
        SER GLN LYS LEU LEU TRP GLN LEU ASN GLY ARG LEU GLU TYR CYS
        TCT CAG AAA CTG CTG TGG CAA CTG AAC GGC CGC CTG GAA TAC TGC 35              40              45
        LEU LYS ASP ARG MET ASN PHE ASP ILE PRO GLU GLU ILE LYS GLN
        CTG AAA GAC CGC ATG AAC TTT GAT ATC CCA GAA GAA ATC AAA CAG 50              55              60
        LEU GLN GLN PHE GLN LYS GLU ASP ALA ALA LEU THR ILE TYR GLU
        CTG CAA CAG TTC CAA AAA GAA GAT GCA GCG CTC ACT ATC TAC GAA 65              70              75
        MET LEU GLN ASN ILE PHE ALA ILE PHE ARG GLN ASP SER SER SER
        ATG CTG CAA AAC ATC TTC GCG ATC TTC CGT CAA GAC TCT TCC TCT 80              85              90
        THR GLY TRP ASN GLU THR ILE VAL GLU ASN LEU LEU ALA ASN VAL
        ACT GGT TGG AAC GAA ACT ATC GTA GAA AAC CTG CTG GCA AAC GTA 95              100             105
        TYR HIS GLN ILE ASN HIS LEU LYS THR VAL LEU GLU GLU LYS LEU
        TAC CAT CAG ATC AAC CAT CTG AAA ACC GTG CTG GAA GAG AAA CTG 110             115             120
        GLU LYS GLU ASP PHE THR ARG GLY LYS LEU MET SER SER LEU HIS
        GAA AAA GAA GAC TTC ACC CGC GGT AAA CTG ATG AGC TCC CTG CAT
```

CHART 3a-continued

IFNX412

IFN—β[IFN—β$^{2-7}$ ⟶ IFN—α$_H$$^{1-5}$] [Cys$^{16}$ ⟶ Ser$^{16}$]

```
                125                 130                 135
        LEU LYS ARG TYR TYR GLY ARG ILE LEU HIS TYR LEU LYS ALS LYS
        CTG AAA CGC TAC TAT GGT CGT ATC CTG CAT TAC CTG AAA GCT AAA 140                 145                 150
        GLU TYR SER HIS CYS ALA TRP THR ILE VAL ARG VAL GLU ILE LEU
        GAA TAC TCT CAC TGC GCA TGG ACT ATT GTA CGC GTT GAA ATC CTG 155                 160                 165
        ARG ASN PHE TYR PHE ILE ASN ARG LEU THR GLY TYR LEU ARG ASN
        CGT AAC TTC TAC TTC ATC AAC CGC CTG ACT GGT TAC CTG CGT AAC
        * * *
        TAA
```

```
        10          20          30          40          50
MCNLSQFLQR—SSNFQSQKLL—WQLNGRLEYC—LKDRMNFDIP—EEIKQLQQFQ—

60          70          80          90          100
KEDAALTIYE—MLQNIFAIFR—QDSSSTGWNE—TIVENLLANV—YHQINHLKTV—

110         120         130         140         150
LEEKLEKEDF—TRGKLMSSLH—LKRYYGRILH—YLKAKEYSHC—AWTIVRVEIL—

160
                                  RNFYFINRLT—GYLRN<
```

CHART 3b

IFNX413

IFN—β[IFN—β$^{2-7}$ ⟶ IFN—α$_2$$^{1-5}$] [Cys$^{16}$ ⟶ Ser$^{16}$]

```
┌── ClaI
│                 5                 10                  15
▼       MET CYS ASP LEU PRO GLN PHE LEU GLN ARG SER SER ASN PHE GLN
(N9)    ATG TGC GAC CTG CTG CAA TTC CTG CAA CGT TCT TCT AAC TTC CAA

XmaIII
                20           ▼    25                 30
        SER GLN LYS LEU LEU TRP GLN LEU ASN GLY ARG LEU GLU TYR CYS
        TCT CAG AAA CTG CTG TGG CAA CTG AAC GGC CGC CTG GAA TAC TGC 35                  40                  45
        LEU LYS ASP ARG MET ASN PHE ASP ILE PRO GLU GLU ILE LYS GLN
        CTG AAA GAC CGC ATG AAC TTT GAT ATC CCA GAA GAA ATC AAA CAG 50                  55                  60
        LEU GLN GLN PHE GLN LYS GLU ASP ALA ALA LEU THR ILE TYR GLU
        CTG CAG CAG TTC CAG AAG GAG GAC GCC GCA TTG ACC ATC TAT GAG 65                  70                  75
        MET LEU GLN ASN ILE PHE ALA ILE PHE ARG GLN ASP SER SER SER
        ATG CTC AGA ACA TC TTT GCT ATT TTC AGA CAA GAT TCA TCT AGC 80                  85                  90
        THR GLY TRP ASN GLU THR ILE VAL GLU ASN LEU LEU ALA ASN VAL
        ACT GGC TGG AAT GAG ACT ATT GTT GAG AAC CTC CTG GCT AAT GTC 95                  100                 105
        TYR HIS GLN ILE ASN HIS LEU LYS THR VAL LEU GLU GLU LYS LEU
        TAT CAT CAG ATA AAC CAT CTG AAG ACA GTC CTG GAA GAA AAA CTG 110                 115                 120
        GLU LYS GLU ASP PHE THR ARG GLY LYS LEU MET SER SER LEU HIS
        GAG AAA GAA GAT TTC ACC AGG GGA AAA CTC ATG AGC AGT CTG CAC 125                 130                 135
        LEU LYS ARG TYR TYR GLY ARG ILE LEU HIS TYR LEU LYS ALA LYS
        CTG AAA AGA TAT TAT GGG AGG ATT CTG CAT TAC CTG AAG GCC AAG 140                 145                 150
        GLU TYR SER HIS CYS ALA TRP THR ILE VAL ARG VAL GLU ILE LEU
        GAG TAC AGT CAC TGT GCC TGG ACC ATA GTC AGA GTG AAA ATC CTA
```

CHART 3b-continued

IFNX413

IFN—β[IFN—β$^{2-7}$ ⟶ IFN—α$_2^{1-5}$] [Cys$^{16}$ ⟶ Ser$^{16}$]

```
                  155                 160                  165
       ARG ASN PHE TYR PHE ILE ASN ARG LEU THR GLY TYR LEU ARG ASN
       AGG AAC TTT TAC TTC ATT AAC AGA CTT ACA GGT TAC CTC CGA AAC
       ***
       TGA
```

```
       10              20              30              40              50
MCDLPQFLQR—SSNFQSQKLL—WQLNGRLEYC—LKDRMNFDIP—EEIKQLQQFQ—

60              70              80              90              100
KEDAALTIYE—MLQNIFAIFR—QDSSSTGWNE—TIVENLLANV—YHQINHLKTV—

110             120             130             140             150
LEEKLEKEDF—TRGKLMSSLH—LKRYYGRILH—YLKAKEYSHC—AWTIVRVEIL—

160
                                                      RNFYFINRLT—GYLRN<
```

Chart 3c
IFNX414

IFN—β[IFN—β$^{3-7}$ ⟶ IFN—α$_2^{2-5}$] [Cys$^{16}$ ⟶ Ser$^{16}$]

ClaI ↓

```
                         5                  10                 15
        MET SER ASP LEU PRO GLN PHE LEU GLN ARG SER SER ASN PHE GLN
(N9)    ATG TCT GAC CTG CCG CAA TTC CTG CAA CGT TCT TCT AAC TTC CAA
```

XmaIII ↓

```
                  20               25                  30
       SER GLN LYS LEU LEU TRP GLN LEU ASN GLY ARG LEU GLU TYR CYS
       TCT CAG AAA CTG CTG TGG CAA CTG AAC GGC CGC CTG GAA TAC TGC 35                 40                  45
       LEU LYS ASP ARG MET ASN PHE ASP ILE PRO GLU GLU ILE LYS GLN
       CTG AAA GAC CGC ATC AAC TTT GAT ATC CCA GAA GAA ATC AAA CAG 50                 55                  60
       LEU GLN GLN PHE GLN LYS GLU ASP ALA ALA LEU THR ILE TYR GLU
       CTG CAG CAG TTC CAG AAG GAG GAC GCC GCA TTG ACC ATC TAT GAG 65                 70                  75
       MET LEU GLN ASN ILE PHE ALA ILE PHE ARG GLN ASP SER SER SER
       ATG CTC CAG AAC ATC TTT GCT ATT TTC AGA CAA GAT TCA TCT AGC 80                 85                  90
       THR GLY TRP ASN GLU THR ILE VAL GLU ASN LEU LEU ALA ASN VAL
       ACT GGC TGG AAT GAG ACT ATT GTT GAG AAC CTC CTG GCT AAT GTC 95                 100                 105
       TYR HIS GLN ILE ASN HIS LEU LYS THR VAL LEU GLU GLU LYS LEU
       TAT CAT CAG ATA AAC CAT CTG AAG ACA GTC CTG GAA GAA AAA CTG 110                115                 120
       GLU LYS GLU ASP PHE THR ARG GLY LYS LEU MET SER SER LEU HIS
       GAG AAA GAA GAT TTC ACC AGG GGA AAA CTC ATG AGC AGT CTG CAC 125                130                 135
       LEU LYS ARG TYR TYR GLY ARG ILE LEU HIS TYR LEU LYS ALA LYS
       CTG AAA AGA TAT TAT GGG AGG ATT CTG CAT TAC CTG AAG GCC AAG 140                145                 150
       GLU TYR SER HIS CYS ALA TRP THR ILE VAL ARG VAL GLU ILE LEU
       GAG TAC AGT CAC TGT GCC TGG ACC ATA GTC AGA GTG GAA ATC CTA 155                160                 165
       ARG ASN PHE TYR PHE ILE ASN ARG LEU THR GLY TYR LEU ARG ASN
       AGG AAC TTT TAC TTC ATT AAC AGA CTT ACA GGT TAC CTC CGA AAC

***
TGA
```

Chart 3c
IFNX414

IFN—β[IFN—β$^{3-7}$ ⟶ IFN—α$_2^{2-5}$] [Cys$^{16}$ ⟶ Ser$^{16}$]

```
         10          20          30          40          50
MSDLPQFLQR—SSNFQSQKLL—WQLNGRLEYC—LKDRMNFDIP—EEIKQLQQFQ—

60          70          80          90         100
KEDAALTIYE—MLQNIFAIFR—QDSSSTGWNE—TIVENLLANV—YHQINHLKTV—

110         120         130         140         150
LEEKLEKEDF—TRGKLMSSLH—LKRYYGRILH—YLKAKEYSHC—AWTIVRVEIL—

160
RNFYFINRLT—GLYRN
```

Chart 3d
IFNX421

IFN—β[IFN—β$^{3-28}$ ⟶ IFN—α$_1^{2-26}$]

ClaI

```
                   5                  10                 15
      MET SER ASP LEU PRO GLU THR HIS SER LEU ASP ASN ARG ARG THR
(N9)  ATG TCA GAT CTT CCA GAA ACC CAT TCT CTC GAC AAC AGA CGT ACC 20                  25                 30
      LEU MET LEU LEU ALA GLN MET SER ARG ILE SER PRO GLU TYR CYS
      CTT ATG CTG CTC GCT CAG ATG AGC CGG ATA TCC CCG GAA TAT TGC 35                  40                 45
      LEU LYS ASP ARG MET ASN PHE ASP ILE PRO GLU GLU ILE LYS GLN
      CTC AAG GAC AGG ATG AAC TTT GAC ATC CCT GAG GAG ATT AAG CAG 50                  55                 60
      LEU GLN GLN PHE GLN LYS GLU ASP ALA ALA LEU THR ILE TYR GLU
      CTG CAG CAG TTT CAG AAA GAG GAC GCC GCA TTG ACC ATC TAT GAG

XhoI
                  65                  70            ↓    75
      MET LEU GLN ASN ILE PHE ALA ILE PHE ARG GLN ASP SER SER SER
      ATG CTC CAG AAC ATC TTT GCT ATT TTC AGA CAA GAT TCC TCG AGC 80                  85                 90
      THR GLY TRP ASN GLU THR ILE VAL GLU ASN LEU LEU ALA ASN VAL
      ACT GGC TGG AAT GAG ACT ATT GTT GAG AAC CTC CTG GCT AAT GTC 95                 100                105
      TYR HIS GLN ILE ASN HIS LEU LYS THR VAL LEU GLU GLU LYS LEU
      TAT CAT CAG ATA AAC CAT CTG AAG ACA GTC CTG GAA GAA AAA CTG 110                 115                120
      GLU LYS GLU ASP PHE THR ARG GLY LYS LEU MET SER SER LEU HIS
      GAG AAA GAA GAT TTC ACC AGG GGA AAA CTC ATG AGC AGT CTG CAC 125                 130                135
      LEU LYS ARG TYR TYR GLY ARG ILE LEU HIS TYR LEU LYS ALA LYS
      CTG AAA AGA TAT TAT GGG AGG ATT CTG CAT TAC CTG AAG GCC AAG 140                 145                150
      GLU TYR SER HIS CYS ALA TRP THR ILE VAL ARG VAL GLU ILE LEU
      GAG TAC AGT CAC TGT GCC TGG ACC ATA GTC AGA GTG GAA ATC CTA 155                 160                165
      ARG ASN PHE TYR PHE ILE ASN ARG LEU THR GLY TYR LEU ARG ASN
      AGG AAC TTT TAC TTC ATT AAC AGA CTT ACA GGT TAC CTC CGA AAC

***
TGA
```

```
         10          20          30          40          50
MSDLPETHSL—DNRRTLMLLA—QMSRISPEYC—LKDRMNFDIP—EEIKQLQQFQ—
```

-continued

Chart 3d
IFNX421

IFN—β[IFN—β³⁻²⁸ ⟶ IFN—α₁²⁻²⁶]

```
        60          70          80          90          100
KEDAALTIYE—MLQNIFAIFR—QDSSSTGWNE—TIVENLLANV—YHQINHLKTV—
       110         120         130         140         150
LEEKLEKEDF—TRGKLMSSLH—LKRYYGRILH—YLKAKEYSHC—AWTIVRVEIL—
       160
RNFYFINRLT—GYLRN
```

Chart 3e

Synthetic IFN—β gene [Cys¹⁷ ⟶ Ser¹⁷]

ClaI ... PstI
```
                         5                              10
              MET SER TYR ASN LEU LEU GLY PHE LEU GLN
  CGA TAA GCT ATG TCT TAC AAC CTG CTG GGC TTC CTG CAG 15                    20
  ARG SER SER ASN PHE GLN SER GLN LYS LEU LEU TRP GLN
  CGT TCT TCT AAC TTC CAA TCT CAG AAA CTG CTG TGG CAA

XmaIII
             25              30                 35
  LEU ASN GLY ARG LEU GLU TYR CYS LEU LYS ASP ARG MET
  CTG AAC GGC CGC CTG GAA TAC TGC CTG AAA GAC CGC ATG

PvuII
           41              45
  ASN PHE ASP ILE PRO GLU GLU ILE LYS GLN LEU GLN GLN
  AAC TTT GAT ATC CCA GAA GAA ATC AAA CAG CTG CAA CAG 50              55                 60
  PHE GLN LYS GLU ASP ALA ALA LEU THR ILE TYR GLU MET
  TTC CAA AAA GAA GAT GCA GCG CTG ACT ATC TAC GAA ATG

NruI             HinfI
   65           71                75
  LEU GLN ASN ILE PHE ALA ILE PHE ARG GLN ASP SER SER
  CTG CAA AAC ATC TTC GCG ATC TTC CGT CAA GAC TCT TCC 80                 85
  SER THR GLY TRP ASN GLU THR ILE VAL GLU ASN LEU LEU
  TCT ACT GGT TGG AAC GAA ACT ATC GTA GAA AAC CTG CTG AccI
   90           95              100
  ALA ASN VAL TYR HIS GLN ILE ASN HIS LEU LYS THR VAL
  GCA AAC GTA TAC CAT CAG ATC AAC CAT CTG AAA ACC GTG SacII
        105              110
  LEU GLU GLU LYS LEU GLU LYS GLU ASP PHE THR ARG GLY
  CTG GAA GAG AAA CTG GAA AAA GAA GAC TTC ACC CGC GGT SacI
  115             122         125
  LYS LEU MET SER SER LEU HIS LEU LYS ARG TYR TYR GLY
  AAA CTG ATG AGC TCC CTG CAT CTG AAA CGC TAC TAT GGT
```

Chart 3e-continued

Synthetic IFN—β gene [Cys$^{17}$ ⟶ Ser$^{17}$]

```
          130              135              140
ARG ILE LEU HIS TYR LEU LYS ALA LYS GLU TYR SER HIS
CGT ATC CTG CAT TAC CTG AAA GCT AAA GAA TAC TCT CAC

MstI
               145                   150
CYS ALA TRP THR ILE VAL ARG VAL GLU ILE LEU ARG ASN
TGC GCA TGG ACT ATT GTA CGC GTT GAA ATC CTG CGT AAC

BstEII
     155              160     ↓           166
PHE TYR PHE ILE ASN ARG LEU THR GLY TYR LEU ARG ASN
TTC TAC TTC ATC AAC CGC CTG ACT GGT TAC CTG CGT AAC

BamHI
     ↓
TER  ↓
TAA GGA TCC
```

R<AMSYNLLGFLQRSSNFQCQKLLWQLNGRLEYCLKDRMNFDIPEEIKQLQQF

QKEDAALTIYEMLQNIFAIFRQDSSSTGWNETIVENLLANVYHQINHLKTVLE

EKLEKEDFTRGKLMSSLHLKRYYGRILHYLKAKEYSHCAWTIVRVEILRNFYF

INRLTGYLRN<GS

Chart 3f

IFNX401

INF—β[IFN—β$^{2-7}$ ⟶ α$_2^{1-5}$]

```
ClaI                  HinfI (lost)
 ↓              5                 10              15
 ↓   MET CYS ASP LEU PRO GLN PHE LEU GLN ARG SER SER ASN PHE GLN
(N9)ATG TGC GAC TTA CCA CAA TTC CTA CAA AGA AGC AGC AAT TTT CAG 20                 25              30
CYS GLN LYS LEU LEU TRP GLN LEU ASN GLY ARG LEU GLU TYR CYS
TGT CAG AAG CTC CTG TGG CAA TTG AAT GGG AGG CTT GAA TAC TGC 35                  40              45
LEU LYS ASP ARG MET ASN PHE ASP ILE PRO GLU GLU ILE LYS GLN
CTC AAG GAC AGG ATG AAC TTT GAC ATC CCT GAG GAG ATT AAG CAG 50                  55              60
LEU GLN GLN PHE GLN LYS GLU ASP ALA ALA LEU THR ILE TYR GLU
CTG CAG CAG TTC CAG AAG GAG GAG GCC GCA TTG ACC ATC TAT GAG 65                  70              75
MET LEU GLN ASN ILE PHE ALA ILE PHE ARG GLN ASP SER SER SER
ATG CTC CAG AAC ATC TTT GCT ATT TTC AGA CAA GAT TCA TCT AGC

80                  85              90
THR GLY TRP ASN GLU THR ILE VAL GLU ASN LEU LEU ALA ASN VAL
ACT GGC TGG AAT GAG ACT ATT GTT GAG AAC CTC CTG GCT AAT GTC 95                 100             105
TYR HIS GLN ILE ASN HIS LEU LYS THR VAL LEU GLU GLU LYS LEU
TAT CAT CAG ATA AAC CAT CTG AAG ACA GTC CTG GAA GAA AAA CTG 110                 115             120
GLU LYS GLU ASP PHE THR ARG GLY LYS LEU MET SER SER LEU HIS
GAG AAA GAA GAT TTC ACC AGG GGA AAA CTC ATG AGC AGT CTG CAC 125                 130             135
LEU LYS ARG TYR TYR GLY ARG ILE LEU HIS TYR LEU LYS ALA LYS
CTG AAA AGA TAT TAT GGG AGG ATT CTG CAT TAC CTG AAG GCC AAG
```

Chart 3f-continued
IFNX401

```
         140                    145                    150
GLU TYR SER HIS CYS ALA TRP THR ILE VAL ARG VAL GLU ILE LEU
GAG TAC AGT CAC TGT GCC TGG ACC ATA GTC AGA GTG GAA ATC CTA 155                    160                    165
ARG ASN PHE TYR PHE ILE ASN ARG LEU THR GLY TYR LEU ARG ASN
AGG AAC TTT TAC TTC ATT AAC AGA CTT ACA GGT TAC CTC CGA AAC

170
* * *
```

```
         10            20            30            40            50
MCDLPQFLQR—SSNFQCQKLL—WQLNGRLEYC—LKDRMNFDIP—EEIKQLQQFQ—

60            70            80            90           100
KEDAALTIYE—MLQNIFAIFR—QDSSSTGWNE—TIVENLLANV—YHQINHLKTV—

110           120           130           140           150
LEEKLEKEDF—TRGKLMSSLH—LKRYYGRILH—YLKAKEYSHC—AWTIVRVEIL—

160
RNFYFINRLT—GLYRN<
```

CHART 4
Nucleotide sequence of trp promoter region of IFN-β expression plasmid pl-24/C

We claim:

1. A modified beta interferon comprising a beta interferon wherein amino acids 2 to 7 of said beta interferon are replaced by amino acids 1 to 5 of alpha 2 interferon.

2. A modified beta interferon comprising a beta interferon wherein amino acids 2 to 7 of said beta interferon are replaced by amino acids 1 to 5 of alpha H interferon polypeptide and the cysteine located at position 17 of natural beta interferon is replaced with serine.

3. A modified beta interferon comprising a beta interferon wherein amino acids 2 to 7 of said beta interferon are replaced by amino acids 1 to 5 of alpha 2 interferon and the cysteine located at position 17 of natural beta interferon is replaced with serine.

4. A modified beta interferon comprising a beta interferon wherein amino acids 3 to 28 of said beta interferon are replaced by amino acids 2 to 26 of an alpha 1 interferon.

5. A modified beta interferon comprising a beta interferon wherein amino acids 3 to 7 of said beta interferon are replaced by amino acids 2 to 5 of alpha 2 interferon and the cysteines located at position 17 of natural beta interferon polypeptide is replaced with serine.

6. A pharmaceutical composition for use in the treatment of viral infections or neoplastic disease or for stimulating the immune system in an animal comprising an effective therapeutic amount of the modified beta interferon of claim 1 admixed with a pharmaceutically acceptable carrier.

7. A pharmaceutical composition for treating viral infections in an animal comprising an effective amount of the modified beta interferon of claim 2 admixed with a pharmaceutically acceptable carrier.

8. A pharmaceutical composition for treating viral infections in an animal comprising an effective amount of the modified beta interferon of claim 3 admixed with a pharmaceutically acceptable carrier.

9. A pharmaceutical composition for treating viral infections in an animal comprising an effective amount of the modified beta interferon of claim 4 admixed with a pharmaceutically acceptable carrier.

10. A pharmaceutical composition for treating viral infections in an animal comprising an effective amount of the modified beta interferon of claim 5 admixed with a pharmaceutically acceptable carrier.

11. A method of treating viral infections in an animal in need of such treatment comprising the administration of an effective amount of a modified beta interferon of claim 1.

12. A method of regulating cell growth in an animal in need of such treatment comprising the administration of an effective amount of a modified beta interferon of claim 1.

13. A method of regulating the immune system in an animal in need of such treatment comprising the administration of an effective amount of a modified beta interferon of claim 1.

* * * * *

UNITED STATES PATENT AND TRADEMARK OFFICE
CERTIFICATE OF CORRECTION

PATENT NO. : 4,738,844
DATED : April 19, 1988
INVENTOR(S) : Bell, et al.

It is certified that error appears in the above-identified patent and that said Letters Patent is hereby corrected as shown below:

Column 4, line 4, reading "$\beta$ and $\alpha$," should read -- $\beta$ and $\alpha_1$ --.

Column 10, line 29, reading "$1:20^5$" should read -- $1:10^5$ --.

Column 10, line 44, reading "0.85% bromophenol blue" should read -- 0.05% bromophenol blue --.

Column 12, line 52, reading "20:1 to 10:1" should read -- 20:1 or 10:1 --.

Columns 17 and 18, Chart 3a, the nucleotide sequence of the codon coding for amino acid LEU at position 56, reading "CTC" should read -- CTG --.

Columns 19 and 20, Chart 3b, the nucleotide sequence of the codon coding for amino acid PRO at position 5, reading "CTG" should read -- CCG --.

UNITED STATES PATENT AND TRADEMARK OFFICE
CERTIFICATE OF CORRECTION

PATENT NO. : 4,738,844
DATED : April 19, 1988
INVENTOR(S) : Bell, et al.

It is certified that error appears in the above-identified patent and that said Letters Patent is hereby corrected as shown below:

Columns 27 and 28, Chart 3e, the fourth line from the bottom, reading "R<AMSYNLLGFLQRSSNFQC" should read
-- R<AMSYNLLGFLQRSSNFQS -- (i.e., the last letter of this section of the chart should be "S" instead of "C").

Columns 27 and 28, Chart 3f, the nucleotide sequence of the codon coding for amino acid ASP at position 53, reading "GAG" should read -- GAC --.

Signed and Sealed this

Thirteenth Day of March, 1990

Attest:

JEFFREY M. SAMUELS

*Attesting Officer*    Acting Commissioner of Patents and Trademarks